United States Patent
Kodukula et al.

(10) Patent No.: US 6,845,336 B2
(45) Date of Patent: Jan. 18, 2005

(54) WATER TREATMENT MONITORING SYSTEM

(76) Inventors: Prasad S. Kodukula, 780 S. Federal St., Suite 907, Chicago, IL (US) 60605; Charles R. Stack, 290 Shadybrook Ln., Aurora, IL (US) 60504

( * ) Notice: Subject to any disclaimer, the term of this patent is extended or adjusted under 35 U.S.C. 154(b) by 54 days.

(21) Appl. No.: 10/179,436

(22) Filed: Jun. 25, 2002

(65) Prior Publication Data

US 2003/0236649 A1 Dec. 25, 2003

(51) Int. Cl.[7] ............................................. G06F 15/00
(52) U.S. Cl. ...................... 702/118; 702/188; 702/104; 702/91; 702/50; 700/48; 700/51; 700/67; 706/6; 706/15
(58) Field of Search ........................... 702/47, 50, 59, 702/91, 104, 188, 189, 193–194, FOR 103, 123, 127, 128; 700/48, 51, 67; 706/6, 15

(56) References Cited

U.S. PATENT DOCUMENTS

| | | |
|---|---|---|
| 4,948,509 A | 8/1990 | Stack |
| 5,106,511 A | 4/1992 | Kodukula |
| 5,498,328 A | 3/1996 | Smith-Haddon |
| 5,646,863 A | 7/1997 | Morton |
| 5,647,986 A | 7/1997 | Nawathe et al. |
| 5,742,500 A | 4/1998 | Irvin |
| 5,779,911 A | 7/1998 | Haug et al. |
| 5,808,916 A | 9/1998 | Orr et al. |
| 5,832,468 A | 11/1998 | Miller et al. |
| 5,848,378 A | 12/1998 | Shelton et al. |
| 5,892,690 A * | 4/1999 | Boatman et al. ............ 700/276 |
| 5,895,565 A | 4/1999 | Steininger et al. |
| 5,943,662 A | 8/1999 | Baba et al. |
| 6,023,223 A | 2/2000 | Baxter, Jr. |
| 6,097,995 A | 8/2000 | Tipton et al. |
| 6,104,963 A | 8/2000 | Cebasek et al. |
| 6,119,125 A | 9/2000 | Gloudeman et al. |
| 6,141,595 A | 10/2000 | Gloudeman et al. |
| 6,154,681 A | 11/2000 | Drees et al. |
| 6,167,316 A | 12/2000 | Gloudeman et al. |
| 6,178,393 B1 | 1/2001 | Irvin |
| 6,625,569 B2 * | 9/2003 | James et al. ................. 702/183 |
| 2002/0049625 A1 * | 4/2002 | Kilambi et al. ................ 705/9 |
| 2002/0116157 A1 * | 8/2002 | Markle et al. .............. 702/188 |
| 2003/0154056 A1 * | 8/2003 | Ito et al. ...................... 702/188 |

OTHER PUBLICATIONS

Lin et al., 'Amino acid substitution matrices from an artificial neural network model', Jun. 2001, Ridgeway, pp. 1–22.*

Mirsepassi et al., 'Application of Artificial Neural Networks to the Real Time Operation of Water Treatment Plants', Jun. 1995, IEEE, pp. 516–521.*

* cited by examiner

Primary Examiner—Marc S. Hoff
Assistant Examiner—Elias Desta
(74) Attorney, Agent, or Firm—John C. McMahon

(57) ABSTRACT

A computer system linked by the internet to various remote waste water treatment facilities. The system receives real-time data from the facilities and analyzing the data to determine likely operational upsets and future effluent water quality. The computer system sends signals to a hierarchy of parties depending on the severity of predicted upsets problems and events. The computer also provides a probability distribution of such upsets and water quality and recommendations as how to adjust facility operating parameters to avoid or reduce the upsets to acceptable parameters and maintain effluent water quality parameters within preselected limits.

26 Claims, 1 Drawing Sheet

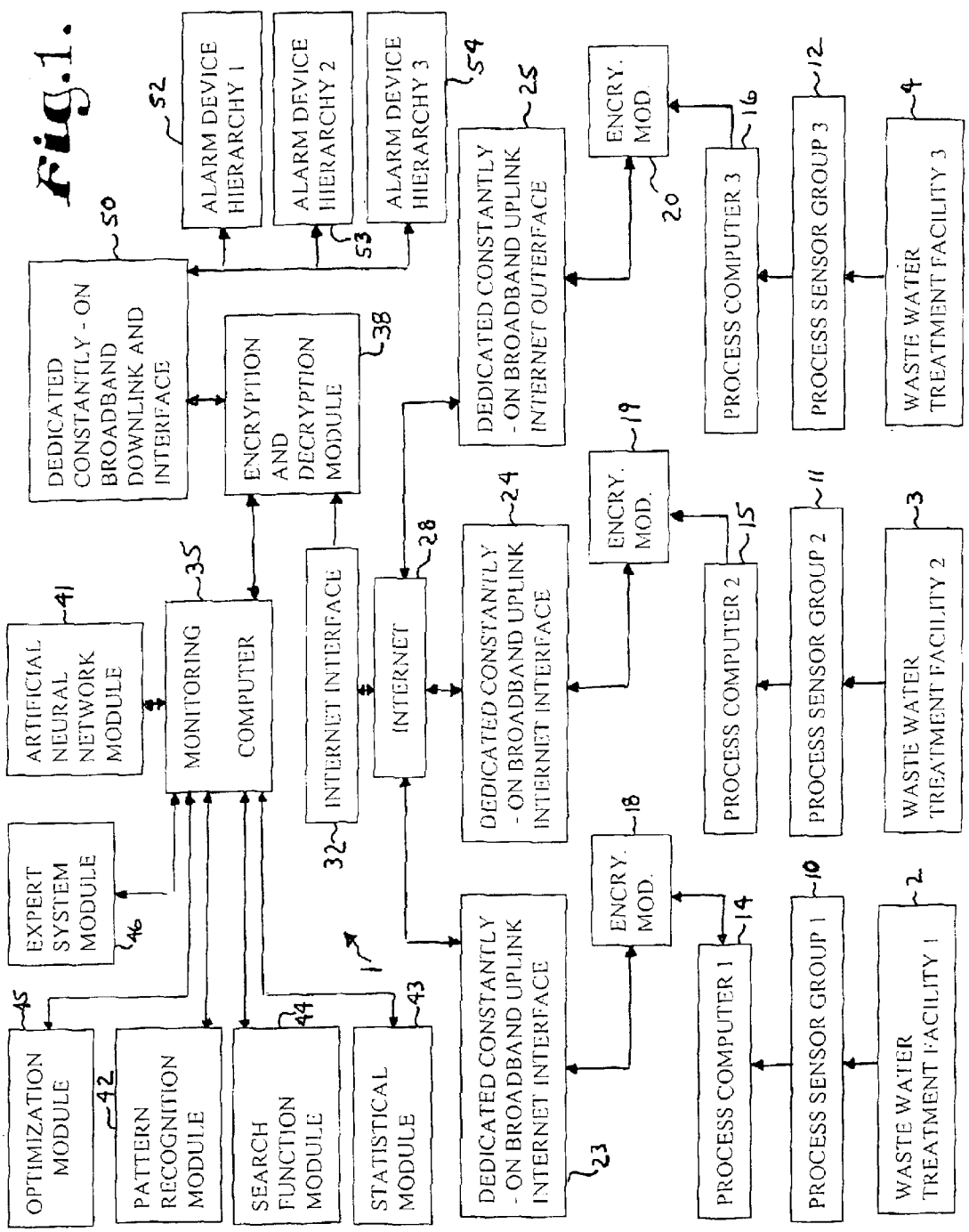

WATER TREATMENT MONITORING SYSTEM

BACKGROUND OF THE INVENTION

The present application is directed to a plurality of wastewater treatment facilities, potable water treatment facilities or the like in combination with a remote monitoring computer system that monitors such facilities, especially via the internet and sends alarm signals to facility personnel when the computer detects or predicts that effluent quality or other measurements either are or will be outside of preselected parameters, predict process failures, and/or determine that the facility could be better optimized. The alarm signals are preferably sent to personnel in a hierarchal process associated with the severity of the problems detected or predicted.

Wastewater treatment plants or facilities are used to treat virtually any water streams containing pollutants that are discharged into rivers, lakes or the like within the United States. Wastewater streams to be treated by such facilities can originate from a wide variety of sources, including industrial plants wherein the water may be polluted with a wide variety of chemicals and municipal sewage where the water may be polluted with large amounts of organic matter and microbes. Almost every waste water treatment facility receives water that is uniquely polluted. Nevertheless, the effluent from each site or facility must meet certain governmental or self imposed regulatory parameters for effluent water quality and all discharged water must be within such quality parameters. Failure to meet the required effluent parameters can result in substantial fines and damages or even criminal sanctions to operators of such plants. More importantly, failure to have the effluent quality within the set parameters may result in damage to public health, damage to a surrounding ecosystem and environment or even loss of human life in severe situations.

Further, fresh water facilities are used to prepare drinking or potable water for use by the public. Such facilities are a major concern with respect to potential tampering and general homeland security.

Water treatment facilities include numerous electronic or readable sensors that provide immediate feedback to operators that indicate to operators the status of various quality parameters within the water at various locations along the treatment process. The effluent water is especially tested either by mechanical sensors or by operators taking and analyzing physical samples. Modifications can be and are made in the overall process when the operators discover that some part of the process is not performing correctly or where effluent quality measurements suggest that the process is not meeting desired quality parameters.

Water treatment facilities are typically complex with numerous tanks, basins or the like that often hold millions of gallons of water and often cost in the tens of millions of dollars. Because of the complexity of the processes at each facility, it is difficult to fully control the process and maintain constant compliance with regulations or operating parameters. Furthermore, unforseen events can occur in the process that lead to problems with effluent quality, but which may not show up immediately at various sensor stations or which may show up too slowly to prevent the entire treatment process from cycling out of control. During such events effluent quality parameters and/or some other critical factors may exceed desired levels and it may take a substantial time to get the entire process back under control. Meanwhile, the facility operators risk discharging water that does not meet quality parameters.

It is also desirable to be able to predict process upsets and failures that may or may not directly effect effluent quality, such as a "bulking" problem in a biological waste water treatment facility that may result in facility shutdown. Further, it is desirable to optimize such processes to reduce costs, for example, when excess air or oxygen is being injected into the water during treatment.

Still further, while facility operators are well trained, it is possible for an operator to commit accidental operating error or even deliberately modify operating conditions to create a problem with the effluent or any water or for an outside party to deliberately sabotage the process.

While facilities often have multiple sensors for various parameters, it is possible that failure of one or more of the sensors may provide results that mislead operators and which eventually cause the effluent to be outside the required quality parameters.

Consequently, it is desirable to have a water treatment facility monitor system which in real-time samples data and continuously reviews sensor outputs and database information from the treatment process throughout a facility to provide backup to the operation of the facility, both at an operator level and at a management level, and to continuously predict effluent water quality based upon sensed real-time operating conditions and historic data, especially where it is difficult for an operator to foresee that various events may culminate in unacceptable effluent water quality or where defective equipment does not give operators advance warning of problems and to predict process upsets or failures while optimizing usage of energy, chemicals and the like.

Further, the monitoring system is preferably off-site and connected in real time by an internet system (which would include or be in some instances an intranet system) to a central computer having an artificial neural network which can simultaneously monitor a plurality of such facilities, each treating water with somewhat different pollutants.

The monitoring system preferably includes an expert system to predict effluent quality problems and process upsets or failures such as bulking, pH exceeding a preselected maximum, or overt toxicity.

Finally, the degree of severity of problems varies greatly from minor to catastrophic. Consequently, such a monitoring system needs to have preselected alarm thresholds for various conditions either directly measured or calculated such that when the computer determines that a trigger, such as an exceeded threshold or predicted future upset, has occurred, then the computer will send one or more alarms through an alarm system to facility personnel and authorities. Preferably, there is a hierarchy set of such thresholds depending upon how much an actual or calculated parameter exceeds the threshold value or depending on how important the parameter is to effluent water quality or surrounding environmental control. For situations where minor or easily corrected problems, associated with effluent quality, process upsets or optimization, are detected, an alarm may be sent to the facility operators. Where problems of a higher nature are noted, alarms may be sent to a first tier of management, to an upper tier of management independent of or in addition to the facility operators, or to government officials.

In this manner, a facility located anywhere on the globe can be monitored by a computer system that is quite advanced and can provide alarms to those having responsibility for the plant should it appear that effluent water quality parameter or another important factor is predicted to be outside selected limits. In this manner, steps can be taken to control or avoid the problem or upset. Further, the computer system can learn over time and with the study of multiple facilities, so as to provide greater expertise and skill in prediction of problems from data representative of process conditions that may not raise a level of concern in an operator.

SUMMARY OF THE INVENTION

Water treatment facilities for treatment of water with various types of chemical, biological or organic pollutants are monitored by an off-site monitoring computer system. It is noted that a single facility can include more than one individual treatment process. Sensor data is collected from various locations within each facility along with information from databases and other input data sources, and fed via constantly-on dedicated broadband communication uplinks, especially through the internet to the monitoring computer through a security module.

The computer includes an artificial neural network module that reviews data to determine its quality and replaces what is considered defective data with a calculated replacement value. The sensors may be a large number of data sources including sensory hardware for measuring process variables such as temperature, pH, carbon dioxide concentration, flows or the like. The sensor inputs may also be detected values of variables from the surrounding environment, such as greenhouse gas (carbon dioxide methane) concentrations or the like. Further, the sensor inputs may be signals that a particular event has occurred or is occurring. For example, a signal may indicate that particular equipment is turned on or off, that a particular liquid level has been exceeded, that more air is being injected than is needed to meet aeration requirements, or that an effluent quality limit (such as maximum pH) is being exceeded. Still further, the sensor inputs may be visual, spoken from an operator, calculated by facility equipment or the like or from a historic or real-time database.

The artificial neural network integrates and cooperates with the other modules of the computer software. It especially learns from past events at a plurality of facilities and in cooperation with the other modules uses the information learned to predict future problems and undesirable situations based upon such learning by applying likely outcomes to incoming data and by accessing the best steps to prevent or limit such future effluent quality problems, process upsets or failures, better optimization methods and similar situations. The artificial neural network also studies the incoming data to identify errors, gaps, invalid reading, sensing equipment failures, other hardware failures and the like. The artificial neural network deletes data that it finds to be obviously in error and replaces such data, where necessary, along with gaps with data that it calculates or predicts from historic data or from other sources which appear to be more correct. The artificial neural network also identifies and filters "noise" from incoming process data.

Operably integrated and working with the neural network is a pattern recognition module that takes various input from the sensors and generated by the neural network and predicts effluent water quality and process upsets which is then compared to preselected desired parameters. This information is utilized to predict when effluent water quality parameters will not be met and when predefined process failure events are likely to occur in each facility.

A statistical module is also integrated with the neural network and evaluates both input data from the sensors and predicted future effluent water quality to calculate the probability distribution of the parameters that are part of the sensor inputs and predicted effluent quality. The statistical module preferably prepares multiple dimensional distribution functions that plot multiple variables and provide a user with a more accurate analysis with respect to problems and the probability of such problems, as compared to a simple two dimensional distribution.

Further, an optimization module is integrated with the neural network and uses the various sensor inputs and information calculated by the neural network to predict desired values for various immediate and near future process operating parameters that are required in the process to maintain quality parameters in the effluent at or below preselected or target values.

An expert system module receives data regarding the current status of various locations along or within the process in a facility both through direct sensor data and calculated data, including expected effluent quality assuming no changes are made to the process, and recommends operator responses that can be made at the facility in order to reduce the likelihood of future process upsets, water quality problems or undesirable situations, both within the process itself and in effluent quality, as well as optimization of expense associated with the process. The expert system module especially suggests process modifications to prevent catastrophic process failure, especially requiring shut down of the process and divergence of influent water, or disastrous and unacceptable effluent water quality. The expert system is also designed to make recommendations as to how to minimize operational costs. Further, the expert system can determine if events are occurring that are outside of a range that can be corrected by its degree of expertise and recommend outside specific experts, especially expert engineers or the like that can assist in resolving the problems.

A search system module continuously reviews and searches the data by other modules of the monitoring computer and generates alarm triggers when the data suggest a quality or environmental parameter will exceed a preselected range or where an in-process parameter is or is predicted to become outside of a preselected range selected for it. The search system module especially searches for process failure events or problems of all types. Such may be noncompliance with regulations associated with the environment surrounding the facility, noncompliance with regulations regarding effluent water quality, undesirable upsets within the facility, unnecessary expenditure or waste of costly chemicals, tampering, or the like. A probability distribution preferably a multidimensional distribution, is calculated with respect to each event generating a threshold trigger alarm, including predicted process failure events.

A constantly on dedicated downlink and interface communicates with a plurality of alarm devices. This can be accomplished through internet interfaces or by direct links such as landlines, satellite based communication pagers and cell phone systems or any suitable form of communication system, preferably such that are continuously available and will immediately notify the receiver of such alarms given the problem or situation. The alarm devices may be any type of communication equipment including telephone, cell phones, PDAs, pagers, panel board annunciators, internet messages, or the like. In certain circumstances the alarm device may also directly operate one or more elements of process equipment, where this is allowed.

The alarm and alarm devices are preferably based upon a hierarchy system wherein different alarm devices and, therefore, different or more personnel, are triggered based upon the degree of severity or concern about the potential problem that generates the alarm. That is, minor upsets or problems that are not likely to have a significant effect on effluent quality or the environment or that may cause only minor process upsets may go to one device such as a computer readout at the facility operator's station or phone of an operator, whereas a major upset that is likely to result in water quality being outside of mandated levels or catastrophic process failure may result in phone and pager messages being sent to the process operator on duty, one or more levels of management and/or government officials.

Where appropriate, operators may also have access to the monitoring computer through the internet or the like to retrieve historic or live information concerning their process or other processes, provided they have been granted access to such information.

Preferably, the computer system with its computer programs is utilized at a centralized site for monitoring a plurality of water facilities at many different remote locations and is adapted to learn from the operating histories of all of the facilities to aid in the operation of each.

The system, including the monitoring computer, of the present invention can thus watch for, predict and help eliminate process failure events and effluent water quality that is outside of desired or required quality parameters. For example, sludge bulking is a common problem in biological wastewater treatment systems. The neural network coupled with the pattern recognition module can sense conditions that may eventually lead to bulking problems. Plant or facility operators are then warned in advance about such process failure events. Furthermore, the computer system will constantly learn about the facility based on historical data, thus continuously getting better at predicting future events. In monitoring a biological wastewater treatment facility, the monitoring computer system has the capability to determine when energy is being wasted. For example, if more injected oxygen or air is being used then is necessary for the process, as determined by sampling or calculation, then the computer can signal to reduce the speed of aeration devices and thereby reduce the energy usage and cost of operation. Further, biological processes require proper input of nutrient for optimum biological activity and chemical process require addition of certain levels of chemicals. The computer can calculate the amount of nutrients (nitrogen, phosphorous, etc) required or the quantity of chemicals required, compare this to actual addition rates of such chemicals and notify the operator the amounts added are too much or too little in comparison to the amount actually needed.

The system of the present invention also watches for situations where process design limits are exceeded by either measured or calculated variables. The system uses triggers and alarms to indicate that such design limits have been exceeded. For example, if dissolved air flotation (DAF) is designed to allow the facility to process a maximum of one million gallons of water per day, then a warning (alarm, etc.) may be provided to the operators when influent flow is expected to exceed this amount. Another key design parameter in biological treatment process is food to microorganism ratio. If the calculated ratio exceeds a preselected threshold value, then an alarm or warning is given to the operators. The system also watches the process and compares operating conditions to optimum performance conditions. When the optimum conditions are not met, a message is given to the operator, preferably with recommendations as to how to better optimize the process. Using predictive and dynamic statistical models, various variables are predicted through probability distribution analysis. The predictions are preferably expressed to the operators as probability distributions. For example, an operator may be informed that there is a 90% probability that the chemical oxygen demand (COD) of the water within or exiting the facility will exceed a maximum desired or required level of 50 milligrams per liter.

The present monitoring system may be used for potable water, wastewater treatment plants cooly tower treatment facilities, boiler water treatment facilities, cleaning systems, fermentors, and the like and the same monitoring system can be used for both with segregation of data. The system may also be used with other types of processing plants facing similar problems in control of effluent, prevention of process upsets and optimization of the process.

OBJECTS AND ADVANTAGES OF THE INVENTION

Therefore, the objects of the present invention are: to provide a remote monitoring system for a fresh water or waste water treatment facility that backs up facility operators and aids in preventing catastrophic failures of the process and the maintenance of effluent water quality within selected parameters and that further calculates and predicts failures, problems and undesirable situations from correct or incorrect data inputs that might not be predicted by an operator without aid of the monitoring system; to provide such a monitoring system that can be used with a plurality of facilities, each with different concentrations of pollutants and each being remote from the others; to provide such a monitoring system wherein data from all types of sensors at a facility is transmitted over secure, constantly on communicator systems to a computer of the monitoring system; to provide such a monitoring system wherein the monitoring computer includes a neural network module, a pattern recognition module, a statistical module, a search function module, an optimization module and an expert system module to fully analyze data inputs, disregard inputs that are apparently in error, predict operation parameters and effluent quality parameters, predict undesirable future events and situations based upon historical patterns, provide a probability distribution of likely future effluent and in-process quality parameters, constantly search data and probability results to find events that may occur that trigger threshold alarms and provide an analysis and recommendation as to what steps can be taken to optimize the process in the future based upon an optimization of present status; to provide such a monitoring system that sends out alarms to persons in response to the threshold alarms; to provide such a monitoring system wherein alarms are sent on a hierarchal basis depending on severity of any projected problem to different persons or to persons who can best handle a particular problem with recommendations on how to avoid or reduce the severity of the problem; and to provide a process for using the monitoring system in combination with waste water facilities.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a schematic view of a plurality of waste water treatment facilities and quality monitoring system in accordance with the present invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a monitoring system in accordance with the present invention. The monitoring system 1 is illustrated in FIG. 1 in use with three waste water treatment facilities 2, 3 and 4. Although the illustrated monitoring system 1 is shown with three facilities 2, 3 and 4, it may be used with a large number of such facilities which would economize with respect to the number of monitoring systems 1 required and which would allow learning and statistical background portions of the system to draw from a wider range of actual operation. The monitoring system 1 could be used with only a single facility. It is also for foreseen that the monitoring system 1 may be utilized with other types of treatment facilities, including but not limited to potable water facilities, boiler water treatment, cooling tower water treatment systems, cleaning systems, fermentors, and the like. As used herein the term facility includes the term system.

Waste water facilities 2, 3 and 4 may be any of a large number of such facilities which take in water that includes inorganic and/or organic pollutants that are a hazard to water sources such as rivers and lakes or that may damage the surrounding environment. The facilities 2, 3 and 4 either remove the pollutants from the water or convert them to a substance that does not present a hazard or danger. Such facilities are especially used where waste water is to be discharged into fresh water drinking sources that provide drinking water to humans.

Such facilities 2, 3 and 4 each normally receive water with substantially different pollutants and so the effluent water to each may vary greatly in types and concentrations of pollutants found in the water. Nevertheless, it is important to bring the effluent water quality exiting each facility 2, 3 or 4 within certain preselected parameters. Effluent water quality is often prescribed or regulated by local and/or national governmental regulations dealing with water quality that is discharged to fresh water supplies. The facilities 2, 3 and 4 use chemicals to treat polluted water or may use microbes for the treatment of water or both. Waste water facilities are well known in the prior art and vary from a single small treatment chamber to very large plants with 10, 12 or more chambers holding millions of gallons. Such facilities may vary greatly in type. Some may be continuous flow type or sequencing batch reactor type. Further, when microbes are utilized for water treatment, such facilities may use aerobic, anaerobic and/or anoxic processes.

Each waste water treatment facility 2, 3 and 4 has data which is generated by a plurality of sensors generally grouped and described herein as process sensor groups 10, 11 and 12. The sensor groups 10, 11 and 12 may develop data from a quite large range of sources, many of which are instruments mounted throughout the facilities 2, 3 and 4 or in the environmental areas around the facilities 2, 3 and 4 or in water streams that are located downstream of the effluent water discharge from the facilities 2, 3 and 4.

The process sensor groups 10, 11 and 12 may also receive data from sources other than hard process or environmental instrumentation. The data may come from laborating instruments or from historical or real-time databases of information collected at each facility 2, 3 and 4. Further, the data may be continuous such as provided by a continuously operating electronic instrument providing temperature, pH, fluid flow or the like; or may be discrete or non continuous such as an indication that a sludge pump is operating or a sludge level is raising; or discrete laboratory test results from process samples taken by facility operators. Still further, the data can be something other than an instrument reading or test result, such as an operator voice record or a plant camera video input. Each process sensor group 10, 11 and 12 represents a wide range of data collected within each respective facility 2, 3 and 4 and may also include data that is stored at a database or generated within a facility using direct sensors or data from other sources.

The data outputs from each sensor group 10, 11 and 12 are linked by appropriate means including hard wired lines, operator data input, radio signals, infrared signals or any other suitable means of transmission to a respective process computer 14, 15 and 16. Although a single computer 14, 15 and 16 is shown for each facility 2, 3 and 4, it is foreseen that numerous computers could be equivalently utilized and that some instrumentation may have integral computers.

For security purposes, each process computer 14, 15 and 16 includes a respective encryption module 18, 19 and 20 wherein data to be sent out of the respective facility 2, 3 or 4 is encrypted and any encrypted data from outside the facility 2, 3 or 4 is decrypted. Encryption and decryption of data is utilized to prevent third parties from tampering with either the data or operation of the facilities 2, 3 and 4.

Each process computer 14, 15 and 16 is maintained active twenty four hours a day during every day the associated facility 2, 3 or 4 is operated. Data from each computer 14, 15 and 16 is continuously transmitted though a respective dedicated constantly-on broadband uplink internet interface 23, 24 and 25 respectively to the internet 28. The interfaces 23, 24 and 25 can be a wide range of communication equipment including modems and the like with associated communication transmission systems such as land based communication links, satellite communication systems and the like that will effectively link communications between the respective process computers 14, 15 or 16 with the internet 28. While the internet 28 is preferred, it is foreseen that a direct communication line could be utilized to link with the monitoring system 1.

A downlink internet interface 32 receives data transmitted by the internet and transmits such data continuously to a monitoring computer 35. The monitoring computer 35 includes an encryption module 38 that decrypts data from the process computers 14, 15 and 16. The monitoring computer 35 preferably receives all data from the process computer continuously and as much as is possible in real-time. Data received from each respective facility 2, 3 or 4 is maintained segregated for that facility and calculations are made throughout the computer 35 for a particular facility. However, all of the data, predicted results, process modifications, actual results, etc. are stored in a database within the computer 35 that allows the computer 35 to learn over time and to develop strategies to handle future problems and operation conditions that appear similar to or related to past problems and operational conditions.

Authorized operators or other facility personnel that are authorized access to the information, data and the like both historical and real time, may access the monitoring computer 35 through the internet or otherwise to obtain such information and data.

The monitoring computer 35 has a number of software modules that are utilized in conjunction with the received process data including an artificial neural network module 41, a pattern recognition module 42, a statistical module 43, a search module 44, an optimization module 45 and an expert system module 46.

The artificial neural network module 41 works in cooperation with the other modules 42 to 46 to analyze the data and perform other functions as described below.

In particular, the artificial neural network module 41 is initially programed to analyze received process data and provide various output. The artificial neural network module 41 reviews the data received from each facility 2, 3 and 4 separately, but can learn from a problem or resolution of a problem at one facility how to predict upsets and prevent such upsets at another facility.

The artificial neural network module 41 first evaluates all of the incoming process data that may include facility operation data and environmental data to determine incoming noise, data gaps, data equality, errors and failures of hardware sensors that may have occurred in the data. The artificial neural network module 41 then uses historic information, data manipulation, data averaging, data from other sensors or the like to provide the best value possible for missing data while eliminating data that is believed to be grossly in error. The resulting modified data is utilized in a number of functions to especially predict process upsets and future effluent water quality parameters, the detection of potential operational problems, especially noncompliance with governmental or self imposed regulation problems, and undesirable process situations including the waste of resources, and recommendations with respect to proactive measures that facility operators can take to resolve such potential problems and situations. The artificial neural network module 41 not only uses hard sensor data form the facilities to make predictions, but also uses soft data as a "soft" sensor that is produced by software calculations from within the computer 38 to make predictions.

The pattern recognition module 42 cooperates with the artificial neural network module 41 and searches the incoming data to find matches with previous data and operational modes (or predicted data where no prior data exists) to locate patterns that are recognized as possibly leading to upsets within the operating processes within the facilities 2, 3 and 4 or to unacceptable quality in the effluent water from the facilities 2, 3 and 4. Previous or potential process failures are defined with parameters that the pattern recognition module 42 tries to find in the incoming data and, when such parameters are found, the pattern recognition module 42 predicts the likely advent of process failure events.

The statistical module 43 also cooperates with the artificial neural network module 41 and collects specific incoming process data and predicted future effluent quality data and uses such to calculate probability distributions for selected parameters that are associated with such data. Preferably, the distributions are multidimensional so as to increase the likelihood that important predictions that result form multiple data or factors will be considered for potential future problems. The distributions are especially useful in helping decision makers evaluate how the downstream treatment process will behave and what parameters to expect, if no changes are made in the operation of the facility, since the future predicted results of water quality based on certain process parameters alone may vary, since the processes are complex, especially with respect to parameters early in the process. Therefore, it is better to make decisions on the basis of most likely future result, keeping in mind that catastrophic events, even with a low likelihood of occurrence, should be carefully watched for so as to insure process conditions do not change that would make them more likely to occur.

The search function module 44 reviews the information predicted by other elements of the computer 35 and in cooperation with the artificial neural network 41 locates any predicted or likely process failure events. The search function module 44 studies the probability distributions and generates threshold alarms based upon present conditions that are compared to the events and distributions to find where future conditions are likely to be undesirable or problematic. Threshold alarms are immediately passed to facility operators or others, as will be described below.

The alarm trigger thresholds may be hard in type wherein a specific sensor value is compared to a preselected range and an alarm is triggered if the value is outside the range or may be soft in type where the computer 35 software calculates and predicts expected values which may result in problems or undesirable situations and which also trigger alarms.

The optimization module studies process parameters and predicted effluent water quality and then uses prior process history, engineering factors and the like to propose process operational changes that will result in better or improved predicted effluent water quality. The expert system module 46 compares current predicted process upsets and effluent water quality problems to prior operations and known process modification steps to identify actions by process operators that will prevent or lessen process upsets and reduce the likelihood of water quality being outside required parameters. The expert system module 46 also studies process operation and proposes changes in facility operation to minimize cost and resource waste without creating water quality problems.

Security is necessary to prevent tampering with data by hackers or third parties. The monitor computer 35 securely communicates through the encryption module 38 with a dedicated constantly on broadband downlink and computer interface 50. The interface 50 in turn communicates with a series of alarm devices 52, 53 and 54. The alarm devices 52, 53 and 54 provide warning to personnel associated with the various waste water facilities that a threshold by a predicted upset of future predicted effluent quality parameter. The alarm devices 52, 53 and 54 operably receive the alarm signals that are generated by the search function module 44 or any other part of the monitoring computer 35. The alarm devices 52, 53 and 54 are hierarchal in nature. The monitoring computer 35 assigns to each warning or alarm signal a hierarchy level of severity, including such levels as mission critical, near mission critical, dangerous and the like. The computer 35 controls each alarm device 52, 53 or 54 dependent on the hierarchy level that is assigned a particular hierarchy level of severity. For example, low level problems may be communicated to plant operators through alarm device 52, more severe problems to plant middle level management through alarm device 53 and the most severe to top management through alarm device 54. In some situations problems and/or recommendations are sent to multiple alarm devices 52, 53 and 54. The overall security of data can be set in accordance with particular needs. In some cases only a particular facility personnel can receive or send data, whereas in others, especially where common ownership or operation exist, alarms or other information regarding more than one facility can be sent to a person. Also, facility personnel can online access the monitoring computer 35 though the encryption modules 18, 19, 20 and 38 to receive additional on historical information about operation of a particular facility, when they have authorization to have access to such information.

The alarm devices 52, 53 and 54 will normally vary for each facility 2, 3 and 4, but may be the same, especially where commonly owned or operated. The alarm devices 52, 53 and 54 will preferably be constantly on and continuously available. The alarm devices may be a wide variety of communication devices including telephones, especially dedicated phones, connected by landlines or satellite, pagers, computers or the like. The alarm devices may be messages or signals sent by return through the internet 32. Alarm signals may be sent through cable, DSL, fiberoptic systems, cellular phones, fixed satellites at any orbit, or other suitable links, especially constantly on and dedicated broadband communications systems of any type suitable. In some situations it may be possible that the alarm devices 52, 53 and 54 perform a proactive function at a facility in combination with communicating, such as turning off a pump.

The monitoring computer 35 may send a variety of signals including potential problems with measured process parameters or predicted parameters, specified actual or predicted process failure events or simply information as to how to better economize operation. The principal purpose of the monitoring computer 35 is to prevent catastrophic failure of the treatment process at a facility 2, 3 or 4, to prevent process failures, to prevent environmental problems and to minimize operational expense.

It is to be understood that while certain forms of the present invention have been illustrated and described herein, it is not to be limited to the specific forms or arrangement of parts described and shown.

What is claimed and desired to be secured by Letters Patent is as follows:

1. In a treatment facility adapted for use with water wherein pollutants are removed from the water and wherein water exiting from the facility has various acceptable and predetermined effluent quality parameters; said facility including a plurality of operational sensors for operably determining process water quality conditions while the water is in the facility; the improvement comprising:
   a) a monitoring computer at a site remote from said facility and including software to receive data from said sensors, analyze the water quality conditions inputted by said sensors and predict effluent water quality and process upsets; said monitoring computer further including an artificial neural network module to determine solutions to actual and potential water quality and process upsets; and
   b) an internet interface operably connecting said computer to said sensors for transferring said process water quality conditions from said sensors to said monitoring computer and transferring said solutions form said monitoring computer to said facility.

2. The facility according to claim 1 including:
   a) an alarm system operably connected to said monitoring computer and receiving alarm messages when future water effluent quality as predicated by said monitoring computer is not within acceptable effluent water quality parameters.

3. The facility according to claim 2 wherein:
   a) said alarm system is linked to alarms directed to personnel associated with said facility.

4. The facility according to claim 3 wherein:
   a) said facility personnel are grouped in at least first and second hierarchal groups; said alarm system having at least first and second alarm trigger thresholds such that, if said monitoring computer predicts process upsets or process failure events of a first preselected severity, then a first alarm notice is sent to said first hierarchal group and, if said monitoring computer predicts process upsets or process failure events of a second preselected severity, then a second alarm notice is sent to said second hierarchal group.

5. The facility according to claim 2 wherein:
   a) said facility is a first facility; and
   b) linking a plurality of additional facilities to said monitoring computer such that said monitoring computer evaluates data from each additional facility and sends alarm signals to each facility when such a facility has a potential future process upset or process failure event.

6. The facility according to claim 1 including:
   a) a process computer linked to and receiving data from said process sensors;
   b) said process computer including an encryption software module for encrypting data sent to said monitoring computer; and
   c) said monitoring computer including a decryption module for operably securely receiving data from said facility.

7. The facility according to claim 1 wherein said monitoring computer includes:
   a) an artificial neural network module for analyzing incoming process data and adjusting such data where necessary; and
   b) said artificial neural network module maintaining historic database of past facility operation and using said database with algorithms to learn how to better prevent or minimize future process upsets and process failure events.

8. The facility according to claim 7 wherein said monitoring computer includes:
   a) a statistical module;
   b) a pattern recognition module; and
   c) a search function module;
   d) such that each module of steps a through c integrate with said artificial neural network module to study incoming data and find likely process upsets and process failure events.

9. The facility according to claim 8 wherein said monitoring computer includes:
   a) an expert system module to provide recommendations as to how to avoid or limit said process upsets and process failure events.

10. The facility according to claim 9 wherein said monitoring computer includes:
    a) an optimization module to propose recommendations to optimize process operation and reduce process operation cost.

11. The facility according to claim 1 wherein:
    a) said facility is a waste water treatment facility.

12. The facility according to claim 1 wherein:
a) said facility is a fresh water treatment facility.

13. A process for real-time monitoring of a water treatment facility comprising the steps of:
a) collecting operational data from said facility;
b) providing a monitoring computer at a remote location from the facility;
c) transferring said data over internet communication lines to the computer;
d) providing software with the monitoring computer to operably analyze the data and to detect ongoing and predict future waste water treatment process failure events; and
e) sending an alarm signal from the monitoring computer to the facility to provide warning of the process failure events.

14. The process according to claim 13 wherein said facility is a first and providing at least one additional facility that is monitored by said monitoring computer.

15. The process according to claim 13 including the step of:
a) linking said computer directly to at least one piece of operating equipment in said facility such that said computer can operably operate said piece of equipment to prevent a process failure event.

16. The process according to claim 13 including the steps of:
a) providing said computer with a historical memory of facility operations;
b) providing said computer with an artificial neural network; and
c) linking said historical memory to said artificial neural network to allow said computer to learn from the historic memory so as to better detect and predict process failure events.

17. A process for real-time monitoring of a water treatment facility comprising the steps of:
a) collecting operational data from said facility;
b) providing a monitoring computer at a remote location from the facility;
c) transferring said data over communication lines to the computer;
d) providing software with the computer to operably analyze the data and predict waste water treatment process upsets and process failure events; and
e) sending a hierarchal alarm signal from the computer to the facility to provide warning of the process upsets and failure events; said alarm signal having a first hierarchy alarm that is sent to a first party in response to an upset or event having a lower degree of severity and a second hierarchy alarm that is sent to a second party in response to an upset or event having a higher severity.

18. The process according to claim 17 including:
a) transmitting said hierarchal alarm signal throughout a wide variety of communications systems to receivers of such signals.

19. A water treatment system including:
a) a plurality of waste water treatment facilities; at least some of said facilities being located at sites remote from one another;
b) each of said facilities having a sensor group having multiple sensors, each of said sensors providing real-time data of parameters associated with operation of each facility and surrounding environment thereof;
c) a monitoring computer located at a site remote from at least some of said facilities;
d) a computer and communication interface adapted respectively for each facility to operably continuously connect with the internet;
e) each of said communication interfaces including encryption software such that transmissions passing through the interfaces into the internet are encrypted for security purposes;
f) said monitoring computer including operational software having an artificial neural network module that receives said data from each facility; said operational software evaluating the received data to determine quality of the received data and using the received data from each facility to predict future operational conditions within the facility;
g) said operational software having a pattern recognition module that cooperates with the neural artificial network module to locate common patterns with historic operation and predict process failure events at each facility;
h) said operational software having a statistical module cooperating with said artificial neural network module to evaluate the data from each of the facilities and predicted future operational conditions of each facility to calculate a probability distribution of parameters that are to be expected in future operational conditions, including effluent water conditions;
i) said computer software including a search module that reviews the probability distributions and compares such to thresholds to see if such thresholds are likely to be exceeded; said search module generating an alarm signal each time a threshold is predicted to be exceeded and with respect to each predicted process failure event; and
j) a communication link between said computer and parties associated with each of said facilities; said computer transmitting each alarm signal to a respective party so as to warn the party that either a threshold is likely to be exceeded or a process failure event is likely to occur.

20. The system according to claim 19 including wherein:
a) each of said facilities has associated therewith a hierarchy of personnel; said computer search function module determining the severity that a threshold is predicted to be exceeded and sending different alarm signals to different personnel in the hierarchy depending on the severity of the threshold that is predicted to be exceeded.

21. The system according to claim 19 wherein:
a) said computer software includes an optimization module that continuously compares predicted facility effluent quality and provides recommended steps to be taken to maintain effluent quality within preselected quality parameters while minimizing facility operational expenses.

22. The system according to claim 19 wherein:
a) said computer software including an expert system module that compares predicted operational upsets and events within each facility to historic operational information so as to identify and propose operational strategies that may be used to prevent such upsets and events and sends such strategies to a facility operator.

23. The system according to claim 19 wherein:
a) said sensors include both soft sensor determination made by said computer and hard sensor measurements made by sensor devices directly measuring some parameters.

24. A process for real-time monitoring of a water treatment facility comprising the steps of:
a) collecting operational data from said facility;
b) providing a monitoring computer at a remote location from the facility;
c) transferring said data over internet communication lines to the computer;
d) providing software with the computer to operably analyze the data, to determine where the facility operation is not being optimized and to develop steps to optimize operation of the facility; and
e) sending a message from the computer to the facility personnel providing steps to take to optimize operation of the facility.

25. The facility according to claim 1 wherein:
a) said monitoring computer includes a statistical module; said statistical module utilizing data received by said monitoring computer to predict effluent water quality and process upsets and failures.

26. The facility according to claim 25 wherein:
a) said statistical module cooperates with said artificial neural network to predict process upsets and failures.

* * * * *